(12) United States Patent
Lee et al.

(10) Patent No.: US 9,244,049 B2
(45) Date of Patent: Jan. 26, 2016

(54) SYSTEM AND METHOD FOR DETECTION OF NUTRITIONAL PARAMETERS IN FOOD ITEMS

(71) Applicant: General Electric Company, Schenectady, NY (US)

(72) Inventors: Yongjae Lee, Latham, NY (US); Aghogho Atemu Obi, Troy, NY (US); Seog Tae Kim, Louisville, KY (US); William Chester Platt, Hagaman, NY (US); James William Bray, Niskayuna, NY (US); Yuri Alexeyevich Plotnikov, Niskayuna, NY (US); Jack Mathew Webster, Colonie, NY (US); Vasile Bogdan Neculaes, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 260 days.

(21) Appl. No.: 13/888,759

(22) Filed: May 7, 2013

(65) Prior Publication Data
US 2014/0331796 A1 Nov. 13, 2014

(51) Int. Cl.
*G01N 33/02* (2006.01)
*G01N 22/00* (2006.01)
*G01N 22/04* (2006.01)

(52) U.S. Cl.
CPC ............. *G01N 33/02* (2013.01); *G01N 22/00* (2013.01); *G01N 22/04* (2013.01)

(58) Field of Classification Search
CPC ....... G01N 22/04; G01N 33/02; H04B 1/7163
USPC .......... 324/637–646; 702/19, 23, 27; 359/356
See application file for complete search history.

(56) References Cited

U.S. PATENT DOCUMENTS

| 4,095,274 A | 6/1978 | Gordon |
| 4,695,693 A * | 9/1987 | Staats et al. .................. 219/748 |
| 4,837,414 A | 6/1989 | Edamula |

(Continued)

FOREIGN PATENT DOCUMENTS

| JP | 59032723 A | 2/1984 |
| JP | 1208622 A | 8/1989 |

(Continued)

OTHER PUBLICATIONS

International Search Report and Written Opinion issued in connection with corresponding PCT Application No. PCT/US2014/032835 on Aug. 21, 2014.

*Primary Examiner* — Hezron E Williams
*Assistant Examiner* — Gedeon M Kidanu
(74) *Attorney, Agent, or Firm* — Dority & Manning, P.A.

(57) ABSTRACT

A system for measuring nutritional parameters of food items is provided. The system includes a holding cavity. The system further includes a sensor assembly that includes a transmitter antenna and at least one receiver antenna. The transmitter antenna is configured to transmit signals to a food item in the holding cavity. The receiver antenna is configured to receive response signals from the food item. The system includes at least one switch coupled to each antenna. The switch, in a first state, is configured to set the sensor assembly to an electric potential equal to that of the holding cavity. In a second state, the switch is configured to couple the sensor assembly to a power source. The system also includes a processing unit to process the signals received to determine the nutritional parameters of the food item.

21 Claims, 3 Drawing Sheets

(56) References Cited

U.S. PATENT DOCUMENTS

| | | | |
|---|---|---|---|
| 5,465,094 A * | 11/1995 | McEwan | 342/28 |
| 5,648,038 A | 7/1997 | Fathi et al. | |
| 6,614,238 B1 * | 9/2003 | Jean et al. | 324/639 |
| 8,330,057 B2 | 12/2012 | Sharawi et al. | |
| 8,873,545 B2 * | 10/2014 | Ozawa | 370/352 |
| 2004/0134903 A1 | 7/2004 | Chun | |
| 2005/0254121 A1 * | 11/2005 | Komiyama et al. | 359/356 |
| 2006/0106546 A1 * | 5/2006 | Roberts et al. | 702/27 |
| 2007/0273507 A1 | 11/2007 | Burchell et al. | |
| 2008/0102175 A1 | 5/2008 | Jeon et al. | |
| 2008/0110242 A1 | 5/2008 | Merkel | |
| 2010/0072386 A1 * | 3/2010 | Harra et al. | 250/395 |
| 2010/0125420 A1 * | 5/2010 | Hyde et al. | 702/19 |
| 2011/0120990 A1 * | 5/2011 | Heimerdinger | 219/702 |
| 2012/0053426 A1 * | 3/2012 | Webster et al. | 600/301 |
| 2012/0274470 A1 | 11/2012 | Sandvick | |
| 2013/0027060 A1 | 1/2013 | Tralshawala et al. | |

FOREIGN PATENT DOCUMENTS

| | | |
|---|---|---|
| JP | 3017425 A | 1/1991 |
| JP | 2010255936 A | 11/2010 |

* cited by examiner

SYSTEM AND METHOD FOR DETECTION OF NUTRITIONAL PARAMETERS IN FOOD ITEMS

BACKGROUND

The present invention relates, generally, to systems for determination of nutritional parameters in food items, and, specifically, to a system and method for non-destructive dynamic determination of nutritional parameters.

Intake of right amount of nutritional parameters from food, along with regular workouts, is of paramount importance in maintaining one's health. Nutritional parameters such as calorie content, protein content, carbohydrate content, mineral contents are important to develop a healthy and balanced diet for an individual. Especially to maintain a person's weight, calorie intake and calorie burning must be properly balanced. The amount of calories burnt is dependent on a person's exercise regimen and/or the amount of physical and mental stress she undergoes every day. To be able to maintain one's weight, the amount of calories burnt by one in a day should be proportional to the amount of calories consumed in the day.

Hence, it becomes important to know calorie content of food items before they are consumed. While most packed food items have calorie content information printed on the packaging, it has also been observed that calorie content of packed food items changes when they are mixed with other food items. Moreover, calorie content of food items such as meat, milk, vegetables varies depending on a portion of the food item being consumed. There is hence a need for a system for dynamic measurement of calorie content when food items are being cooked, or when they are being stored, or when they are being kept in containers for consumption.

Current systems for determination of nutritional parameters of food items include placing a food item in a sampling station and exposing the food item to microwaves. However, such systems require that the sampling station is filled completely with the food item. Owing to difference in size and shape of food items, it is not always feasible to fill the same sampling station completely with different kind of food items. For effective usage of such systems different sampling stations are required thus increasing the cost of utilization of the systems. Moreover, these systems cannot be utilized for food items that include more than one ingredient. To measure the nutritional parameters of food items that include more than one ingredient, in current systems, each ingredient must be separated and measured in the sampling station.

The problem pertaining to non-destructive determination of nutritional parameters is solved by placing parameter detection sensors in a holding cavity. To further reduce the space requirements of systems for determination of nutritional parameters, the sensors are placed in already existing devices, such as microwave ovens or electric heaters, which have a cavity defined in them. However, metallic bodies of the sensors may lead to arcing problems when the microwave oven is being used for cooking the food items. Arcing in microwave ovens has known to cause serious damage to microwave ovens.

Hence, there is a need for a system and method that allows for non-destructive measurement of nutritional parameters of the food item without leading to arcing in the microwave ovens.

BRIEF DESCRIPTION

In one embodiment, a system for measuring nutritional parameters of food items is provided. The system includes a holding cavity. The system further includes a sensor assembly that includes a transmitter antenna and at least one receiver antenna. The transmitter antenna is configured to transmit signals to at least a portion of a food item disposed in the holding cavity. The at least one receiver antenna is configured to receive response signals from the food item. Furthermore, the system includes at least one switch coupled to each antenna of the sensor assembly. The switch, in a first state, is configured to set the sensor assembly to an electric potential equal to that of the holding cavity. In a second state, however, the switch is configured to couple the sensor assembly to a power source. The system also includes a processing unit configured to process the signals received by the receiver antenna to determine the nutritional parameters of the food item.

In another embodiment, a system for measuring nutritional parameters of food items is provided. The system includes a holding cavity. The system further includes a sensor assembly that includes a transmitter antenna and at least one receiver antenna. The transmitter antenna is positioned on one side of the cavity and is configured to transmit signals to at least a portion of a food item disposed in the holding cavity. The receiver antenna, on the other hand, is positioned on another side of the cavity that is proximate to the transmitter antenna and is configured to receive response signals from the food item. The system further includes a plurality of metallic shields disposed between the transmitter antenna and the cavity and the receiver antenna and the cavity. The metallic shields are configured to absorb radiation in the holding cavity that is directed towards the transmitter antenna and the receiver antenna. The system also includes a switch coupled to each antenna of the sensor assembly. The switch is configured to place the sensor assembly at a same electric potential as the holding cavity in a first state and to connect the sensor assembly to a power source in a second state. The system for measurement of nutritional parameters also includes a processing unit configured to process the signals received by the receiver antenna to determine the nutritional parameters of the food item.

In yet another embodiment, a method for determination of nutritional parameters in food items is provided. The method includes connecting a transmitter antenna to a power source to transmit signals. The transmitter antenna, which is disposed on one side of a holding cavity, is connected to the power source by changing a state of a switch from a first state to a second state. The method further includes the step of transmitting sensing signals so as to be incident on a food item placed in the holding cavity. Furthermore, the method includes the step of acquiring at least a part of response signals at a receiver antenna that is placed on another side of the holding cavity that is proximate to that which holds the transmitter antenna. Further, the method includes determining a plurality of factors based on an analysis of the reflections acquired by the receiver antenna. The nutritional parameters of the food item are determined based on a relationship between the plurality of factors and the plurality of nutritional parameters.

DRAWINGS

Other features and advantages of the present disclosure will be apparent from the following more detailed description of the preferred embodiment, taken in conjunction with the accompanying drawings which illustrate, by way of example, the principles of certain aspects of the disclosure.

DETAILED DESCRIPTION

Figure 1:
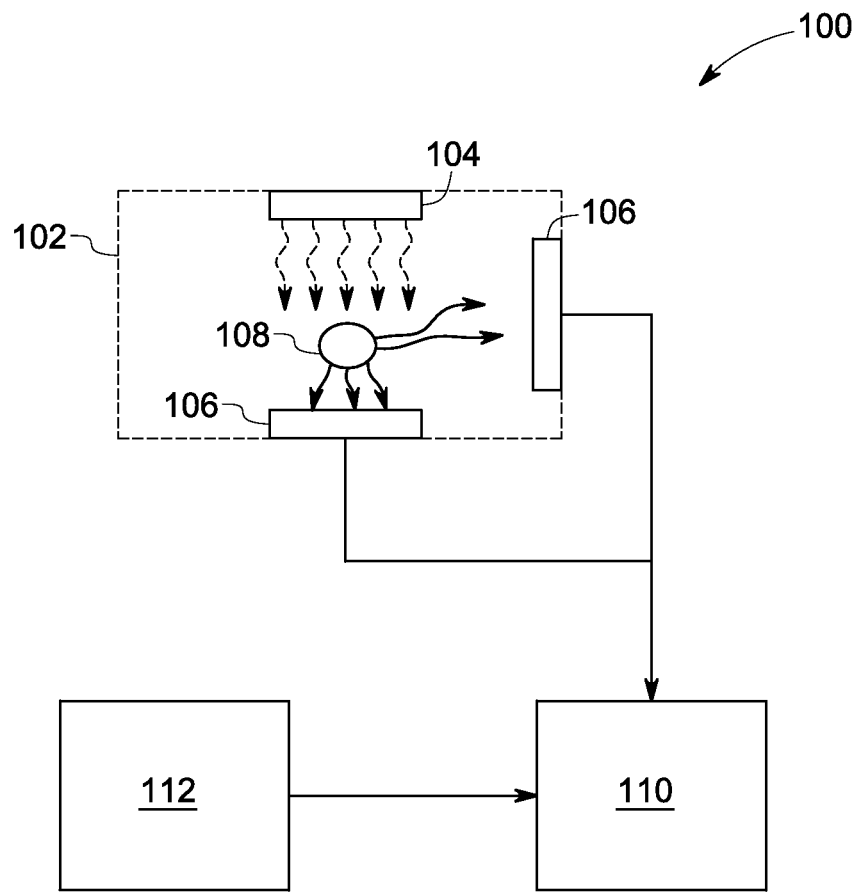
FIG. 1 is an illustration of a system for measurement of nutritional parameters in a food item, according to one embodiment of the present invention.

Reference will be made below in detail to exemplary embodiments of the invention, examples of which are illustrated in the accompanying drawings. Wherever possible, the same reference numerals used throughout the drawings refer to the same or like parts.

As will be discussed in greater detail below, embodiments of the present invention provide for a system for determination of nutritional parameters of food items. A food item, owing to multiple ingredients in it, and by its inherent nature, supplies multiple nutritional parameters to consumers. Nutritional parameters such as energy, carbohydrates, proteins, vitamins, minerals etc. are generally present in every food item. For a balanced diet, it is important to know the quantity of nutritional parameters present in each food item being consumed. To serve this purpose, the system for determination of nutritional parameters in food items can be utilized. The system for determination of nutritional parameters may be a standalone unit. In other embodiments, the system may be integrated into existing appliances, such as but not limited to, microwave ovens and refrigerators. The system includes a holding cavity. The holding cavity is disposed such that it can hold the food item being tested for determination of nutritional parameters. In case the system is integrated into existing appliances, the holding cavity may be the cavity defined in the appliances. For example, in case of a microwave oven, the holding cavity may be the heating cavity of the microwave oven. A sensor assembly, which includes a transmitter antenna and at least one receiver antenna, is placed in the holding cavity such that the transmitter antenna transmits sensing signals onto the food item placed in the holding cavity and the receiver antenna acquires at least a part of sensing signals reflected by the food item, and at least a part of the sensing signals that propagate through the food item. A switch is coupled to each of the transmitter antenna and the receiver antenna. The switch is configured to place at least one of the antennas at the same electric potential as that of the holding cavity in one state of operation. In another state of operation, the switch connects the transmitter antenna to a power source that supplies power to the antenna to enable transmission of sensing signals. The reflections acquired by the receiver antenna are analyzed by a processing unit that is communicably coupled with the receiver antenna. The processing unit is configured to determine a plurality of factors from the reflections. Further, the processing unit is also configured to determine a relationship between the plurality of factors and the nutritional parameters. The relationship between the factors and nutritional parameters is utilized by the processing unit to determine nutritional parameters pertaining to the food item placed in the holding cavity.

FIG. 1 is an illustration of a system for measurement of nutritional parameters in a food item, according to one embodiment of the present invention. The system 100 for measurement of nutritional parameters includes a holding cavity 102. The holding cavity 102, according to one embodiment, may be defined by heat insulating material. In case the system 100 is integrated in existing appliances, the holding cavity 102 may be at least one cavity present in the appliance. Food item 108 being tested for nutritional parameters is placed in the holding cavity 102. The food item 108 may be placed directly in the holding cavity 102. Alternatively, the food item 108 may be placed on a dish (not shown) or a platform (not shown) in the holding cavity 102. The system 100 further includes a sensor assembly that includes a transmitter antenna 104 and at least one receiver antenna 106. The transmitter antenna 104 is configured to transmit sensing signals on to the food item 108. The transmitter antenna 104, according to one embodiment, is configured to transmit ultra-wide band (UWB) signals to at least a portion of the food item 108. According to certain embodiments, the transmitter antenna 104 is configured to transmit sharp or narrow pulse sensing signals. For example, the transmitter antenna 104 is configured to transmit sensing signals of pulse width less than 100 picoseconds. The food item 108 interacts with the sensing signals transmitted by the transmitter antenna and causes the sensing signal to be distorted, reflected, delay, and attenuated. At least some parts of the signals reflected by, or passing through or both are acquired by a receiver antenna 106. The receiver antenna 106 is disposed on at least one side of the holding cavity 102. In one embodiment, more than one receiver antenna 106 may be disposed in the holding cavity 102. One of the receiver antennae 106 may be configured to collect sensing signals reflected from the food item 108. The other receiver antennas 106 may be configured to collect sensing signals passing through the food item 108.

The response signals collected by the receiver antenna 106 are then transmitted to the processing unit 110. The receiver antenna 106 and the processing unit 110 are communicably coupled to each other. According to one embodiment, the processing unit 110 and the receiver antenna 106 are coupled through wired or wireless communication channels. The processing unit 110 is configured to analyze the response signals and determine the nutritional parameters of the food item 108. The processing unit 110 is further communicably coupled with a data repository 112. The data repository 112 provides the processing unit 110 with information required for determination of the nutritional parameter.

The processing unit 110, in certain embodiments, may comprise a central processing unit (CPU) such as a microprocessor, or may comprise any suitable number of application specific integrated circuits working in cooperation to accomplish the functions of a CPU. The processing unit 110 may include a memory. The memory can be an electronic, a magnetic, an optical, an electromagnetic, or an infrared system, apparatus, or device. Common forms of memory include hard disks, magnetic tape, Random Access Memory (RAM), a Programmable Read Only Memory (PROM), and EEPROM, or an optical storage device such as a re-writeable CDROM or DVD, for example. The processing unit 110 is capable of executing program instructions, related to the system for determining nutritional parameters in food items. Such program instructions will comprise a listing of executable instructions for implementing logical functions. The listing can be embodied in any computer-readable medium for use by or in connection with a computer-based system that can retrieve, process, and execute the instructions. Alternatively, some or all of the processing may be performed remotely by additional processing unit 110.

The transmitter antenna 104, according to one embodiment, may be disposed on one side of the holding cavity 102 facing the space where the food item 108 will be placed. The receiver antenna 106, according to certain embodiments, may be placed on the opposite side of the holding cavity 102 than the transmitter antenna 104. In certain embodiments, when more than one receiver antenna 106 is used, receiver antennas may be placed either on the side opposite than the transmitter antenna 104, or on a side adjacent to the transmitter antenna 104, or on the same side as that of the transmitter antenna 104. In the embodiment illustrated in FIG. 1, two receiver antennas 106 have been displayed. One of the receiver antennas 106 is placed opposite to the transmitter antenna 104, and the other receiver antenna 106 is placed on a side that is adjacent to the transmitter antenna 104. In the illustrated embodiment, the receiver antenna 106 that is opposite is configured to receive response of the food item 108 to the sensing signals passing through it. The receiver antenna 106 that is adjacent to the transmitter antenna 104 is configured to gather reflections of the sensing signals from the food item 108.

In certain embodiments, a single antenna may act as both the transmitter antenna 104 and the receiver antenna 106. Such transceiver antennae, when disposed in the holding cavity 102, are configured to transmit sensing signals and acquire at least a part of the reflected sensing signals and sensing signals passing through the food item 108. The food item 108 is exposed to sensing signals from all sides where the transceiver antennae 104 and 106 are placed, and response signals from the food item 108 are received by the transceiver antennae 104 and 106 in the form of reflections to sensing signals or transmissions through the food item 108. Further, in certain embodiments, one of the transmitter antenna 104 and the receiver antenna 106 may be a transceiver antenna.

The transmitter antenna 104 and the receiver antenna 106, according to one embodiment, are planar antennas. The planar antenna may comprise a spiral antenna. The transmitter and receiver antennae may also be achieved by utilizing a plurality of spiral antennae. The planar antenna may comprise different shapes and sizes. The antennae 104 and 106, according to certain embodiments, may be circular, elliptical, rectangular, triangular, bow-tie shaped, or any other known geometrical or irregular shape. In certain embodiments, the antennae 104 and 106 may comprise patch antennae. The patch antennae used as antennae 104 and 106 may include a patch of metal disposed over a sheet of conductive material. The metal patch and the sheet of conductive material may be disposed on a dielectric material.

According to certain embodiments, the transmitter antenna 104 and the receiver antenna 106 may be configured to translate and/or rotate. The transmitter antenna 104 and the receiver antenna 106 may be translated or rotated to allow for scanning of the food item 108 from multiple directions. Also, rotation of the transmitter antenna 104 allows for irradiation of the food item 108. Scanning and irradiation of the food item 108 in the holding cavity 102 allows for spatially oriented nutritional parameter determination in the holding cavity 102. Thus, the system 100 can be used to determine nutritional parameter of more than one food item in a single step.

In one embodiment, when the processing unit 110 is configured to determine calorie content of the food item 108, the data repository 112 is configured to provide the processing unit 110 with information related to a plurality of factors. Plurality of factors include, but are not limited to, water content of the food item 108 and fat content of the food item 108. The plurality of factors stored in the data repository 112 may be acquired dynamically by other peripheral systems coupled with the system 100 such as a weighing device, temperature measuring device and the like.

The system 100 may also be communicably coupled with a user interface (not shown) or other systems where the nutritional parameters of the food item 108 in the system 100 may be utilized. For example, the processing unit 110 may be configured to communicate the nutritional parameter information of the food item 108 to a health management module that enables a user to keep track of his or her weight, nutritional parameters consumed, and effect of the nutritional parameters on vital health statistics of the user. The processing unit 110 may communicate with the external systems through wired or wireless communication channels.

Figure 2:
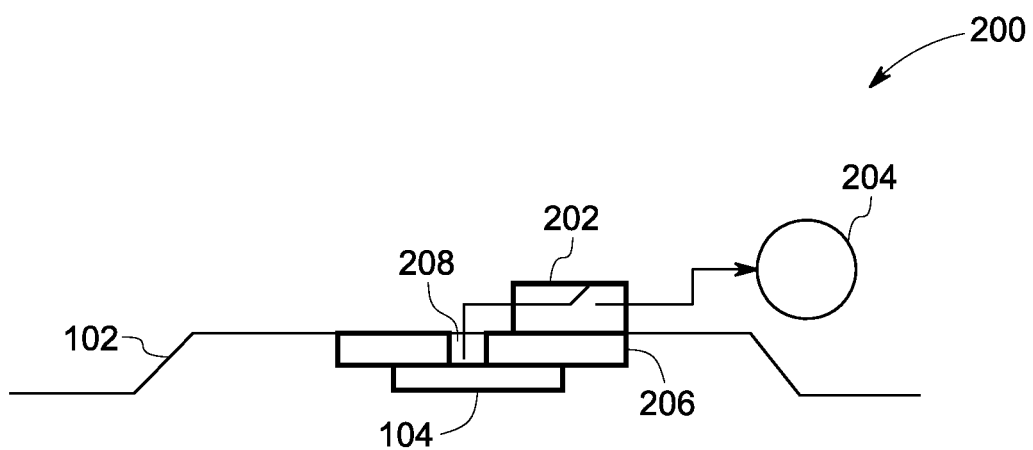
FIG. 2 is an illustration of a system for measurement of nutritional parameters in a food item, according to another embodiment of the present invention.

FIG. 2 is an illustration of a system for measurement of nutritional parameters in a food item, according to another embodiment of the present invention. FIG. 2 illustrates a portion of the holding cavity 102 that is configured to hold the food item 108 for determination of nutritional parameters. In the illustrated embodiment, the transmitter antenna 104 is disposed on one of the sides of the holding cavity 102. The receiver antenna 106 (not shown in FIG. 2) is disposed on at least one of the other sides of the holding cavity 102 such that the antenna 106 collects response of the food item 108 to the sensing signals transmitted by the transmitter antenna 104. In order to allow users of the system for measurement of nutritional parameters dynamically, a switch 202 is coupled with the transmitter antenna 104. The receiver antennae 106 may also be coupled with the switch 202. The switch 202, according to one embodiment, may be any one of known switches that are configured to switch from one state of operation to another state. Examples of switches include, but are not limited to, electromechanical switches, optical switches, electronic switches, and the like. The switch 202 is configured to connect the transmitter antenna 104 to a power source 204.

When the system for determination of nutritional parameters is fitted in existing electronic appliances such as a microwave oven, there may be a possibility of electromagnetic waves of the appliance to interact with a metallic portion of the antennae 104, and 106. The transmitter antenna 104 is disposed on an insulating substrate 206 to avoid the metallic portion of the transmitter antenna 104. Examples of insulating substrate 206 include dielectric material such as, but not limited to, fluoropolymer, strontium titanate, silicone, quartz, pyrex glass, and paper. The substrate 206 separates the metallic portion of the antenna 104 from the holding cavity 102. The receiver antenna 106 (not shown in FIG. 2) may also be disposed on another substrate 206 before being disposed in the holding cavity 102.

The switch 202 is coupled with the antenna 104 through at least one aperture 208 made in the substrate 206. Electric connections from the switch 202 run through the aperture 208 to the metallic portion of the transmitter antenna 104. The electric connections of the switch 202 with the transmitter antenna 104 provide to switch the antenna 104 from being at the same potential as that of the holding cavity 102 to being connected with the power source 204. The switch 202 is configured to keep the antennae 104 and 106 at a same electrical potential as that of the holding cavity 102 to avoid interaction with the electromagnetic waves. The switch 202, according to one embodiment, is configured to place the transmitter antenna 104 at the same electric potential as the walls of the holding cavity 102 in a first state of operation. In a second state of operation, the switch 202 connects the transmitter antenna 104 to the power source 204. According to one embodiment, an "on" or "closed" state of the switch 202 is configured to connect the transmitter antenna 104 to the power source 204 and an "off" or "open" state of the switch 202 is configured to place the antenna 104 at the same electric potential as that of the holding cavity 102. In another embodiment, the transmitter antenna 104 is placed at the same electric potential as that of the holding cavity 102 in an "on" state of the switch 202 and the antenna 104 is coupled to the power source 204 in an "off" state of the switch 202.

According to certain embodiments, the receiver antenna 106 of FIG. 1 is disposed on substrate 206. Apertures in the substrate 206 are utilized to couple antenna 106 with the switch 202.

According to one embodiment, the switch 202 is toggled from a first state that places the antennae 104, and 106 at the same electric potential as that of the holding cavity 102 to a second state that couples the antennae 104 and 106 with the power source 204 when a user may want to utilize the holding cavity for purposes such as cooking, heating, or baking the food item 108.

Figure 3:
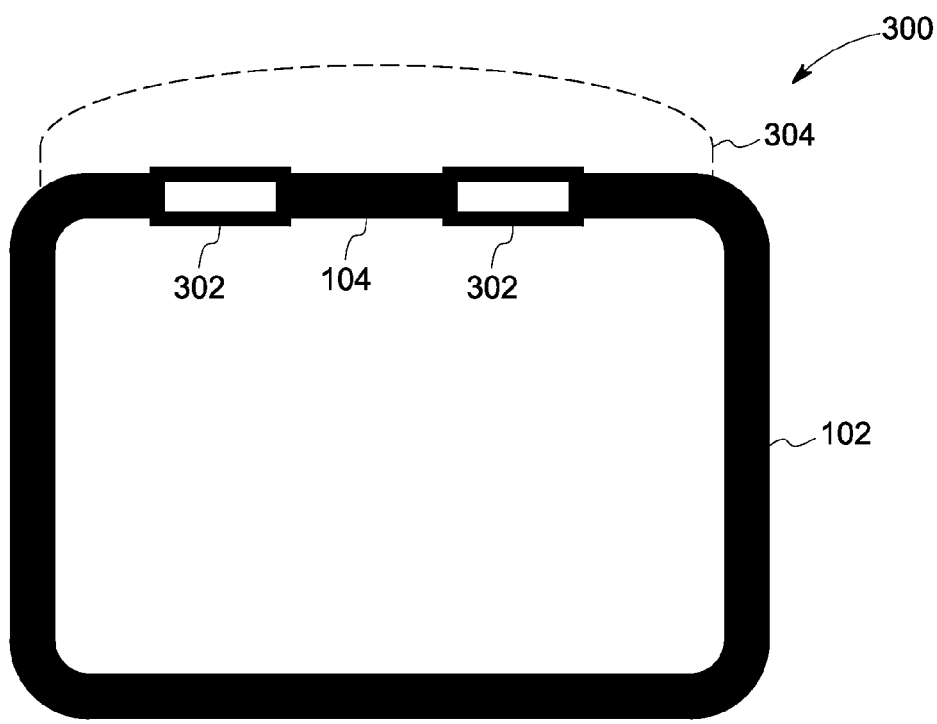
FIG. 3 is an illustration of a system, which includes dielectric material, for measurement of nutritional parameters in a food item, according to another embodiment of the present invention.

FIG. 3 is an illustration of a system 300, which includes dielectric material, for measurement of nutritional parameters in a food item, according to another embodiment of the present invention. The system 300 for measurement of nutritional parameters includes the holding cavity 102, transmitter antenna 104, receiver antenna 106 (not shown), layer of dielectric material 302, and a metallic shield 304. The transmitter antenna 104 and the receiver antenna 106, according to certain embodiments, are aligned along an inner surface of at least one side of the holding cavity 102. The sides of the holding cavity 102 and the antennae 104 and 106, according to certain embodiments, are separated by at least one layer of dielectric material 302. The dielectric material 302, as discussed in conjunction with FIG. 2, is an insulating material. Examples of the dielectric material 302 include, but are not limited to, fluoropolymer, strontium titanate, silicone, quartz, pyrex glass, and paper.

Further, the metallic shield 304 in the system 300 is configured to absorb electromagnetic waves that may escape through the layer of dielectric material 302. The metallic shield 304 is placed such that it seals the holding cavity 102 from all ends without allowing for electromagnetic waves to leave the confines of the holding cavity 102.

The system 300, according to one embodiment, includes a switch that is coupled with the antenna 104. The switch is configured to place the antenna 104 at the same potential as that of the holding cavity 102 in a first state and is configured to connect the antenna 104 to a power source in a second state. The switch and the antenna 104 may be coupled through electrical connections that run from the switch to the antenna 104 through apertures made in the layer of dielectric material 302.

Figure 4:
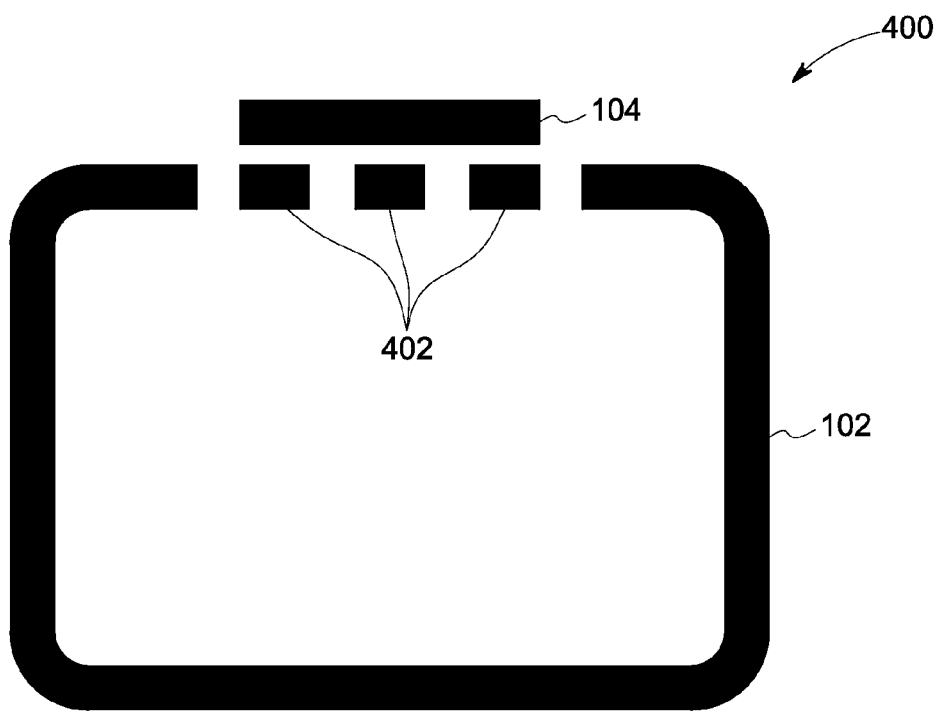
FIG. 4 is an illustration of a system, which includes metallic shields, for measurement of nutritional parameters in a food item, according to yet another embodiment of the present invention.

FIG. 4 is an illustration of a system 400 for measurement of nutritional parameters in a food item, according to yet another embodiment of the present invention. In addition to the holding cavity 102, transmitter antenna 104, receiver antenna 106, switch 202, insulating substrate 206, the system 400 includes metallic shields 402. The metallic shields 402 are disposed proximate to that side of the transmitter antenna 104 that is facing inwards of the holding cavity 102.

According to one embodiment, the metallic shield 402 has a mesh structure. The metallic shield 402 is configured to allow signals transmitted by the transmitter antenna 104 to be incident on the food item 108 placed in the holding cavity 102, while stopping the electromagnetic waves in the cavity 102 from being in direct contact with the transmitter antenna 104.

Figure 5:
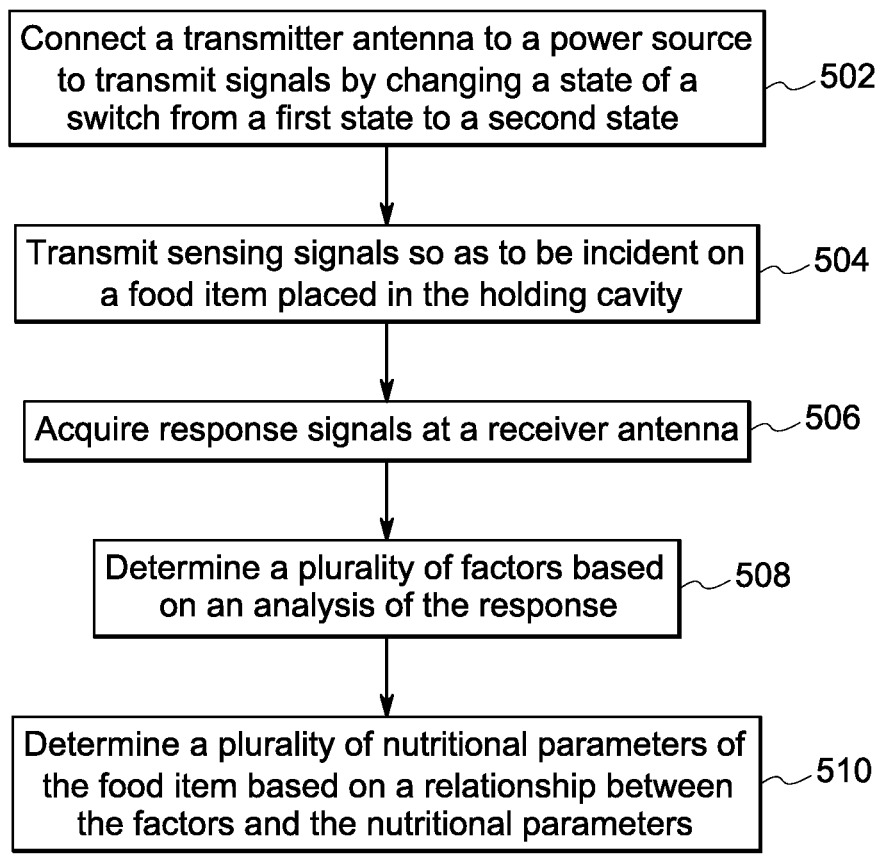
FIG. 5 is a block diagram of a method for determining nutritional parameters of a food item according to one embodiment of the present invention.

FIG. 5 is a block diagram of a method for determining nutritional parameters of a food item 108 according to one embodiment of the present invention. The method includes, at 502, connecting the transmitter antenna 104 to the power source 204 to transmit sensing signals to be incident on the food item 108 placed in the holding cavity 102. The transmitter antenna 104 is disposed on at least one side of the holding cavity 102. At 504, the transmitter antenna 104 transmits Ultra Wide Band (UWB) waves that are incident on the food item 108. The transmitted sensing signals interact with the food item 108 and generate response signals. Response signals, according to certain embodiments, are reflections of the incident sensing signals, or part of sensing signals that passes through the food item 108. At step 506, the response signals are acquired by at least one receiver antenna 106 that is placed along other sides of the holding cavity 102. The receiver antennae 106 are disposed in the holding cavity such that at least a portion of the response signals are acquired.

At step 508, the response signals acquired by the receiver antenna 106 are analyzed to determine a plurality of factors associated with the food item 108. The plurality of factors associated with the food item 108, according to one embodiment, include, but are not limited to, water content of the food item 108, and fat content of the food item 108. The response signals acquired by the receiver antenna 106 are communicated to the processing unit 110. The processing unit 110, based on a comparison between the transmitted sensing signal and the acquired response signals determines the plurality of factors.

At step 510, the processing unit 110 determines the nutritional parameters of the food item 108 from the plurality of factors. The processing unit 110 determines a relationship between the plurality of factors and the nutritional parameters. According to certain embodiments, the processing unit 110 receives historical information from the data repository 112 to build the relationship between the factors and the nutritional parameters. Various techniques such as regression analyses and multivariate analyses may be employed by the processing unit 110 to determine the relationship between the plurality of factors and the nutritional parameters. According to certain embodiments, the processing unit 110 may employ methods disclosed in earlier filed U.S. patent application Ser. Nos. 12/873,067, and 13/193,887.

Experimental comparison between systems for measurement of nutritional parameters without the presence of a switch and/or metallic shields and systems for measurement with the presence of switch and/or metallic shields show that the electric field observed on the sides of the holding cavity 102 on which the antennae 104 and 106 were disposed is higher when the antennae are not grounded during electromagnetic radiation usage. In the experimental setup, when a patch was used as antennae 104 and 106 in the holding cavity 102 and the antennae were not grounded, the electric field strength observed on the sides of the holding cavity 102 with the antennae 104 and 106 was approximately 14 kV/m. When the antennae 104 and 106 in the holding cavity were grounded using the switch 202, during usage of the holding cavity 102 for electromagnetic wave based cooking, the electric field strength observed for the patch antennae 104 and 106 was approximately 8 kV/m. The electric field strength observed on the sides of the holding cavity 102 also decreased with an increase in a number of apertures 208 in the substrate 206. In another experimental setup, dipole antennae, such as a bow-tie antenna, were used as antennae 104 and 106. When the dipole antennae were not grounded, the electric field strength observed on the sides of the holding cavity 102 was observed to be approximately 84 kV/m. When the antennae were connected to ground potential, the electric field strength observed on the sides of the holding cavity 102 was approximately 4 kV/m.

Aforementioned embodiments of system for measurement of nutritional parameters of food items allow for measurement of nutritional parameters in food items without having to move food items out of existing electric appliances. Moreover, the invention reduces the interaction between metallic elements of the antennae and electromagnetic radiation present in the holding cavity. The system provides for provisions to place the antennae at the same electric potential as that of the holding cavity when the cavity is being used for other purposes, while the antennae are connected to a power source when the antennae are being used to determine nutritional parameters.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example. Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet, and may use a wide variety of different communication protocols. Those skilled in the art will appreciate that such network-computing environments will typically encompass many types of computer system configurations, including personal computers, handheld devices, multi-processor systems, microprocessor-based or programmable consumer electronics, network PCs, mini-computers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described system for determination of nutritional parameters in food items, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A system for measuring nutritional parameters of food items, the system comprising: a holding cavity; a sensor assembly comprising a transmitter antenna and at least one receiver antenna, wherein the transmitter antenna is configured to transmit signals to at least a portion of a food item disposed in the holding cavity, and wherein the at least one receiver antenna is configured to receive response signals from the food item; at least one switch coupled to each antenna of the sensor assembly; wherein, in a first state, the at least one switch is configured to set the sensor assembly to an electric potential equal to that of the holding cavity in order to limit interaction between electromagnetic waves in the holding cavity and the sensor assembly; and, in a second state, the at least one switch is configured to couple the sensor assembly to a power source during operation of the sensor assembly to determine the nutritional parameters of the food item; and a processing unit configured to process the signals received by the receiver antenna to determine the nutritional parameters of the food item.

2. The system as recited in claim 1, wherein at least one surface of the transmitter antenna is aligned along an inner surface of at least one side of the holding cavity.

3. The system as recited in claim 2, wherein a metallic element of the transmitter antenna is separated from the at least one side of the holding cavity by a layer of dielectric material.

4. The system as recited in claim 3, further comprising at least one aperture, defined by the layer of dielectric material, through which the at least one switch is connected to the transmitter antenna.

5. The system as recited in claim 3, wherein the dielectric material comprises fluoropolymer, strontium titanate, silicone oil, quartz, pyrex glass, or paper.

6. The system as recited in claim 1, wherein the first state comprises an open state of the switch.

7. The system as recited in claim 1, wherein the second state comprises a closed state of the switch.

8. The system as recited in claim 1, wherein each of the transmitter antenna and the receiver antenna comprises a planar antenna.

9. The system as recited in claim 8, wherein the planar antenna has a circular shape, an elliptical shape, a rectangular shape, or a square shape.

10. The system as recited in claim 1, wherein the transmitter and the receiver antenna comprise a dipole antenna.

11. The system as recited in claim 10, wherein the dipole antenna comprises a bow-tie shaped antenna.

12. The system as recited in claim 1, wherein the sensor assembly comprises metallic shields proximate to sides of the transmitter antenna and the receiver antenna facing the holding cavity.

13. The system as recited in claim 12, wherein the metallic shields has a mesh structure configured to allow signals transmitted by the transmitter antenna to be incident on the food items in the holding cavity.

14. The system as recited in claim 1, wherein the processing unit is configured to determine a water content of the food item, a fat content of the food item, or both from the signals collected by the receiver antenna.

15. The system as recited in claim 14, wherein the processing unit utilizes a relationship between the water content, fat content and a calorie content of the food item to determine the calorie content of the food item.

16. A system for measuring nutritional parameters of food items, the system comprising: a holding cavity; a sensor assembly comprising a transmitter antenna and at least one receiver antenna, wherein the transmitter antenna is positioned on one side of the holding cavity and is configured to transmit signals to at least a portion of a food item disposed in the holding cavity, and wherein the at least one receiver antenna is positioned on another side of the holding cavity that is proximate to the transmitter antenna and is configured to receive response signals from the food item; a plurality of metallic shields disposed between the transmitter antenna and the holding cavity and the receiver antenna and the holding cavity;

wherein the plurality of metallic shields are configured to absorb radiation in the holding cavity that is directed towards the transmitter antenna and the receiver antenna; a switch coupled to each antenna of the sensor assembly, and configured to place the sensor assembly at a same electric potential as the holding cavity in a first state in order to limit interaction between electromagnetic waves in the holding cavity and the sensor assembly and to connect the sensor assembly to a power source in a second state during operation of the sensor assembly to determine the nutritional parameters of the food item; and a processing unit configured to process the signals received by the receiver antenna to determine the nutritional parameters of the food item.

17. The system as recited in claim 16, wherein the plurality of metallic shields have a metallic mesh structure to allow for signals transmitted by the transmitter antenna to be incident on the food item in the holding cavity.

18. The system as recited in claim 16, wherein the first state comprises an open state of the switch, and the second state comprises a closed state of the switch.

19. The system as recited in claim 16, wherein the first state comprises a closed state of the switch, and the second state comprises an open state of the switch.

20. The system as recited in claim 16, wherein the processing unit is configured to determine a water content of the food item, a fat content of the food item, or both from the signals collected by the receiver antenna.

21. The system as recited in claim 20, wherein the processing unit utilizes a relationship between the water content, fat content and a calorie content of the food item to determine the calorie content of the food item.

* * * * *